(12) United States Patent
Butka et al.

(10) Patent No.: US 10,268,989 B2
(45) Date of Patent: Apr. 23, 2019

(54) MEDICAL DEVICE DATA PLATFORM

(71) Applicant: Murj, Inc., Santa Cruz, CA (US)

(72) Inventors: Richard Todd Butka, Santa Cruz, CA (US); Christopher Steven Irving, Santa Cruz, CA (US); Patrick Beaulieu, San Jose, CA (US)

(73) Assignee: Murj, Inc., Santa Cruz, CA (US)

( * ) Notice: Subject to any disclaimer, the term of this patent is extended or adjusted under 35 U.S.C. 154(b) by 171 days.

(21) Appl. No.: 15/134,130

(22) Filed: Apr. 20, 2016

(65) Prior Publication Data
US 2016/0306929 A1 Oct. 20, 2016

Related U.S. Application Data

(60) Provisional application No. 62/149,960, filed on Apr. 20, 2015.

(51) Int. Cl.
*G06Q 10/10* (2012.01)
*G16H 10/60* (2018.01)
*G06F 19/00* (2018.01)

(52) U.S. Cl.
CPC ......... *G06Q 10/1095* (2013.01); *G06F 19/00* (2013.01); *G16H 10/60* (2018.01)

(58) Field of Classification Search
CPC .. G06Q 50/22; G06Q 10/087; G07F 17/0092; G07F 11/62; G07G 1/0045; A61B 50/10; A61B 90/90; A61B 2050/105
See application file for complete search history.

(56) References Cited

U.S. PATENT DOCUMENTS

| | | | | |
|---|---|---|---|---|
| 4,783,803 A * | 11/1988 | Baker | ..................... | G10L 15/00 704/252 |
| 2001/0039504 A1* | 11/2001 | Linberg | .............. | G06F 19/3418 705/3 |
| 2001/0051765 A1* | 12/2001 | Walker | .................. | A61B 5/1112 600/300 |
| 2005/0021370 A1* | 1/2005 | Riff | ..................... | G06F 19/3418 705/2 |
| 2005/0278140 A1* | 12/2005 | Wang | ................. | G01R 31/2894 702/179 |
| 2009/0187426 A1* | 7/2009 | Kerstna | .............. | A61N 1/37282 705/3 |
| 2010/0134353 A1* | 6/2010 | van Diggelen | ......... | G01S 19/05 342/357.66 |

(Continued)

OTHER PUBLICATIONS

International Search Report and Written Opinion, PCT/US2016/028470, dated Jul. 22, 2016.

*Primary Examiner* — Neal Sereboff
(74) *Attorney, Agent, or Firm* — Polsinelli PC

(57) ABSTRACT

Example medical device data platforms are disclosed herein. In an example, the platform may include at least one integration device to access information originating from a plurality of implantable medical devices manufactured by a plurality of manufacturers and implanted in a plurality of patients. The system may also include an information processor to process the accessed information to generate at least one of patient-oriented information and provider-oriented information. The system may also include at least one communication device providing at least one of a patient portal and a provider portal to provide the patient-oriented information and the provider-oriented information, respectively.

21 Claims, 5 Drawing Sheets

(56) References Cited

U.S. PATENT DOCUMENTS

| | | | |
|---|---|---|---|
| 2011/0119212 A1* | 5/2011 | De Bruin | A61B 5/00 |
| | | | 706/12 |
| 2012/0095300 A1* | 4/2012 | McNair | A61B 5/021 |
| | | | 600/300 |
| 2012/0143017 A1* | 6/2012 | Snyder | G06N 20/00 |
| | | | 600/300 |
| 2012/0223889 A1* | 9/2012 | Medlock | G06F 3/04883 |
| | | | 345/168 |
| 2012/0288881 A1* | 11/2012 | Liu | G01N 33/6893 |
| | | | 435/7.92 |
| 2012/0290599 A1* | 11/2012 | Tian | G06F 16/313 |
| | | | 707/758 |
| 2013/0317852 A1* | 11/2013 | Worrell | G06F 19/3418 |
| | | | 705/3 |
| 2015/0227691 A1* | 8/2015 | Bhattacharya | G06N 7/005 |
| | | | 705/3 |
| 2016/0246931 A1* | 8/2016 | Rajan | G06N 7/005 |

\* cited by examiner

MEDICAL DEVICE DATA PLATFORM

CROSS REFERENCE TO RELATED APPLICATION

The present application incorporates in its entirety and claims the benefit under 35 U.S.C. § 119(e) of: U.S. Provisional Application 62/149,960 filed Apr. 20, 2015 and titled Medical Device Data Platform.

FIELD OF THE INVENTION

The present disclosure relates to data processing systems. More specifically, the present disclosure relates to a medical device data platform.

BACKGROUND OF THE INVENTION

Many current implantable medical devices, such as, for example, implantable cardiac devices (e.g., cardiac pacemakers, implantable cardioverter defibrillators (ICDs), implantable loop recorders (ILRs), and so on) include a wireless communication interface whereby information relating to the operation of the device (e.g., diagnostic information) may be regularly or periodically transmitted outside the body of the patient periodically to a separate computing system or device for analysis. This information may then, in some instances, form the basis for one or more changes in the programming of the device to improve the operation of the device. Generally, each device manufacturer employs its own proprietary data format for the information being accessed from the device, as well as for any data being provided to a care provider that summarizes that information.

In some examples, the patient may travel to a medical clinic, an office associated with the manufacturer of the device, or another site to facilitate accessing of the information from the device using a special-purpose programming device. Alternatively, medical personnel may travel to the home of the patient with the programming device to perform the accessing, analysis, and programming operations.

In other instances, a remote monitor associated with the particular manufacturer may be installed in the home of the patient so that the remote monitor may access the information and forward it over a communication interface (e.g., the Internet) to a server operated by the manufacturer. The manufacturer server may then provide that information on a website accessible by medical personnel at a medical clinic or other site for analysis or review. If a device programming change is then advised, the patient may then be requested to travel to the clinic or office, or trained personnel may be directed to the home of the patient with the required equipment, to effect the programming changes.

With the above aspects in mind, as well as others not explicitly discussed herein, various embodiments of a medical device data access system are disclosed herein.

SUMMARY

In one embodiment, a medical device data platform may include at least one integration device configured to access information originating from a plurality of implantable medical devices manufactured by a plurality of manufacturers and implanted in a plurality of patients, an information processor configured to process the accessed information to generate at least one of patient-oriented information and provider-oriented information, and at least one communication device. The at least one communication device may provide at least one of a patient portal and a provider portal. The patient portal may be configured to provide, to each of the plurality of patients, at least a portion of the patient-oriented information corresponding to at least one of the plurality of implantable medical devices associated with the patent. The provider portal may be configured to provide, to each of a plurality of care providers, at least a portion of the provider-oriented information corresponding to at least one of the plurality of implantable medical devices associated with a patient of the care provider. In other examples, such a system may be extended to access data from medical devices that are not implanted within the human body.

While multiple embodiments are disclosed, still other embodiments of the present disclosure will become apparent to those skilled in the art from the following detailed description, which depicts and describes illustrative embodiments. As will be realized, the invention is capable of modifications in various aspects, all without departing from the scope of the present invention. Accordingly, the drawings and detailed description are to be regarded as illustrative in nature and not restrictive.

DETAILED DESCRIPTION

The following detailed description relates to a medical device data platform. In one example, a medical device data platform may include at least one integration device configured to access information (e.g., diagnostic information) originating from a plurality of implantable medical devices manufactured by a plurality of manufacturers and implanted in a plurality of patients. Such implantable medical devices may include, for example, implantable cardiac devices. The medical device data platform may also include an information processor configured to process the accessed information to generate patient-oriented information and/or provider-oriented information. Moreover, the platform may include at least one communication device that may provide at least one of a patient portal and a provider portal. The patient portal may be configured to provide, to each of the plurality of patients, at least a portion of the patient-oriented information for at least one of the plurality of implantable medical devices associated with the patent. The provider portal may be configured to provide, to each of a plurality of care providers, at least a portion of the provider-oriented information for at least one of the plurality of implantable medical devices associated with a patient of the care provider.

As a result of at least some of the embodiments discussed in greater detail below, diagnostics and related information from implantable medical devices manufactured by a plurality of manufacturers, each of which may provide its own proprietary data in a unique format, may be processed to provide information that is tailored to patients and/or care providers (e.g., doctors, nurses, technicians, etc.) regardless of the manufacturer of the particular device. Further, automating the accessing and processing of the data may relieve the manufacturer and/or the care provider of at least some of the data processing and analysis tasks with which they are currently burdened. Other aspects and potential advantages of the embodiments disclosed herein are also presented below.

Figure 1:
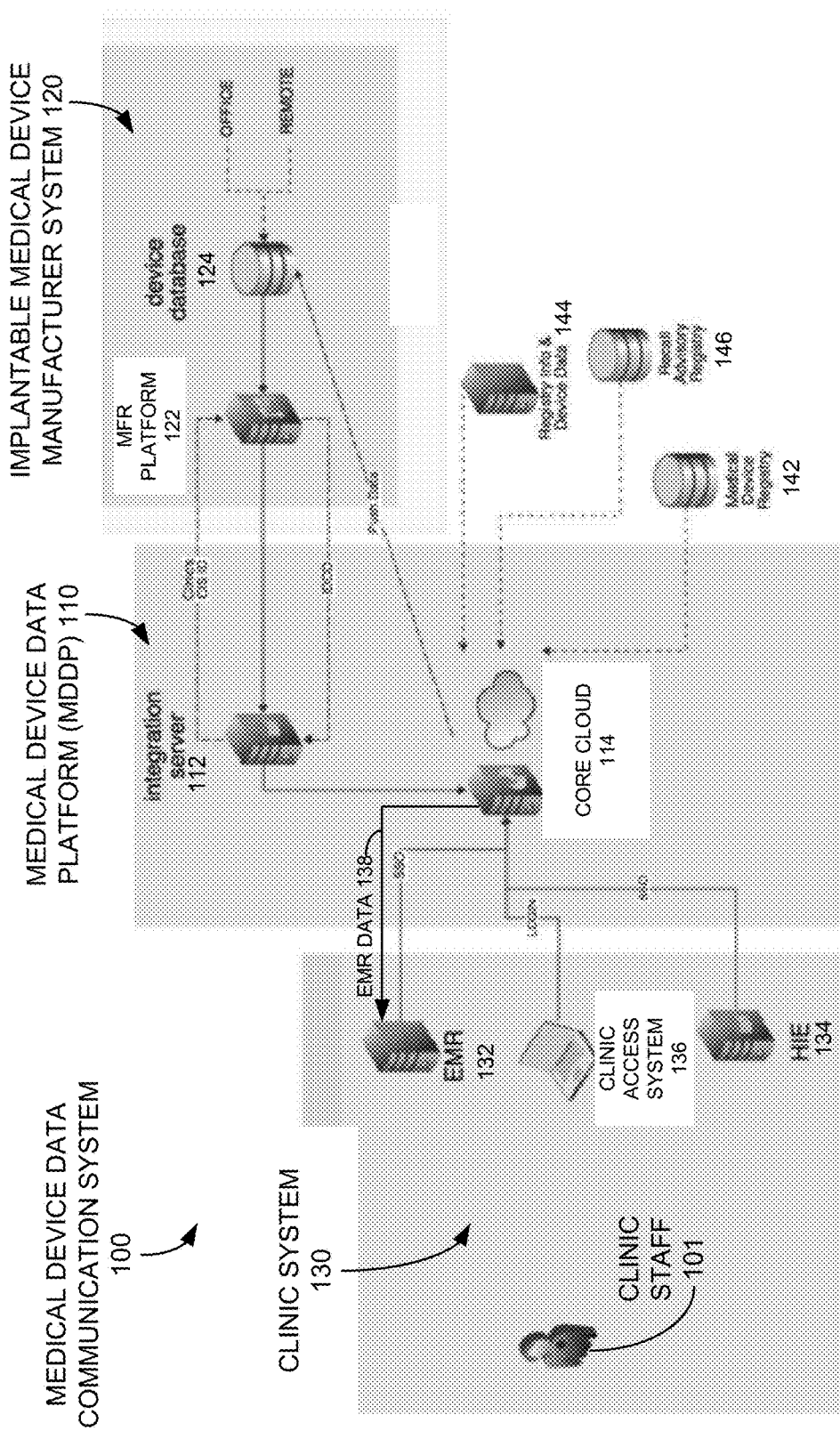
FIG. 1 is a block diagram of a medical device data communication system including an example medical device data platform.

FIG. 1 is a block diagram of a medical device data communication system 100 including an example medical device data platform (MDDP) 110 in communication with multiple implantable medical device manufacturer systems 120 and multiple clinic systems 130. The MDDP 110 may be communicatively coupled with the manufacturer systems 120 and the clinic systems 130 via a wide area network (WAN), such as, for example, the Internet. In some embodiments, each of the manufacturer systems 120 may be associated with a unique implantable medical device manufacturer. In other examples, each of the manufacturer systems 120 may be associated with a unique pairing of an implantable medical device manufacturer and a particular medical clinic or office. In the example of FIG. 1, the manufacturer system 120 may include a manufacturer platform 122, such as, for example, a web server, that retrieves from a device database 124 diagnostic and related data previously uploaded from a plurality of implantable medical devices. Such data may have been retrieved previously from the various implantable medical devices by way of a clinic or office, or by way of a remote monitor, as described above.

The MDDP 110, as depicted in FIG. 1, may include an integration server 112 that accesses the diagnostic and related data for the implantable medical devices from each of the manufacturer systems 120. In an example, the integration server 112 may provide a clinical information system (CIS) identifier associated with a particular clinic to the manufacturer platform 122 to retrieve the diagnostic data and related information, which may be in the form of Implantable Device Cardiac Observation (IDCO) messages. In some embodiments, messages between the integration server and the manufacturer platform 122 may be in the form of alternative, enhanced, or augmented data messages. For example, IDCO messages often contain information formatted as summary reports in Portable Document Format (PDF). In other examples, IDCO-like messages may provide more detailed or "raw" data, such as numerical and/or graphical electrogram (EGM) data regarding arrhythmia or other cardiac episodes detected by the implantable device in integer, floating-point, or another data format. Such information may facilitate easier and/or more detailed processing of the device data within the MDDP 110, as described below.

The integration server 112 may then process the retrieved information to generate patient-oriented information and/or provider-oriented information. In some examples, the retrieved information from the various implantable medical devices may be processed into a format that is unified or generalized across all manufacturers and/or devices of a particular type. While the integration server 112 is depicted in FIG. 1 as a single server, more than one server or computer system may serve as the integration server 112.

The integration server 112 may then forward the processed information to a core cloud 114 that may provide one or more web portals for the clinic systems 130 as well as individual patient communication systems not depicted in FIG. 1. In other examples, the integration server 112 may forward the retrieved device data to the core cloud 114, which may then operate as in information processor to process the data as described above. The core cloud 114 may also generate and provide analytics and other advanced information based on the processed information via the web portals. The core cloud 114, in some examples, may include multiple computer devices or systems configured to perform the various operations ascribed herein to the core cloud 114.

As illustrated in FIG. 1, clinic staff 101 (e.g., one or more doctors, nurses, technicians, etc.) may employ a corresponding clinic system 130 to retrieve the processed device information, possibly including the analytics and other advanced information mentioned above. In some examples, the clinic system 130 may include a clinic access system 136 (e.g., a desktop computer, a laptop computer, a tablet computer, a smart phone, etc.) from which the clinic staff 101 may access a web portal provided by the core cloud 114 to retrieve provider-oriented information. As shown in FIG. 1, the clinic system 130 may also include one or more of an electronic medical records (EMR) system 132 configured to store and facilitate access to EMRs of the patients of the clinic, and a health information exchange (HIE) system 134 configured to exchange health and medical information for the patients of the clinic with other computing systems external to the clinic system 130. In one embodiment, a member of the clinic staff 101 may sign on or log on to the core cloud 114, the EMR system 132, and/or the HIE system 134 using a single sign-on (SSO) procedure, thus reducing the amount of time normally required by the staff 101 member to access each of these systems individually.

In some examples, the integration server 112 may retrieve the device diagnostic data and other device information via a communication connection with one or more of the implantable medical devices, thus possibly reducing the need for one or more of the manufacturer systems 120. In those examples and others, the integration server 112 and/or the core cloud 114 may forward or "push" the unprocessed and/or processed device information, as well as the analytics and other advanced information to one or more of the manufacturer systems 120 for use by the corresponding manufacturers of the devices.

As depicted in FIG. 1, the core cloud 114 may also communicate with, retrieve data from, and/or transmit data to, other systems external to the MDDP 110. For example, the core cloud 114 may access a medical device registry 142 to supply data regarding the efficacy and/or safety of, patient response to, and other information regarding the use of, the various implantable medical devices. The core cloud 114 may also access the device registry data to correlate that data with the processed information received from the various implantable medical devices associated with the core cloud 114.

The core cloud 114 may also access a registry information and device data system 144 configured to track accurately each of the implantable medical devices associated with the core cloud 114. For example, the core cloud 114 may employ data obtained from the registry information and device data system 144 to correlate or associate accurately the information associated with one or more of the implantable medical devices that is processed within the core cloud 114 with the data retrieved from the medical device registry 142.

In some examples, the core cloud 114 may access a recall advisory registry database 146 to retrieve product recall data for an array of implantable medical devices, including those devices associated with the MDDP 110. Further, the core cloud 114 may inform clinic staff 101 via the clinic access system 136 and/or patients via their respective web portals of any recalls involving their corresponding implantable medical devices in a timely manner. Such data may be pushed to the clinic staff 101 or patient via the web portal, email, text, or other communication means. In one example, the MDDP 110 may include the recall advisory registry database 146, and may populate the recall advisory registry database 146 with data from a variety of sources, such as, for example, official federal governing bodies, state or national medical boards, news agencies, and so forth.

Figure 2:
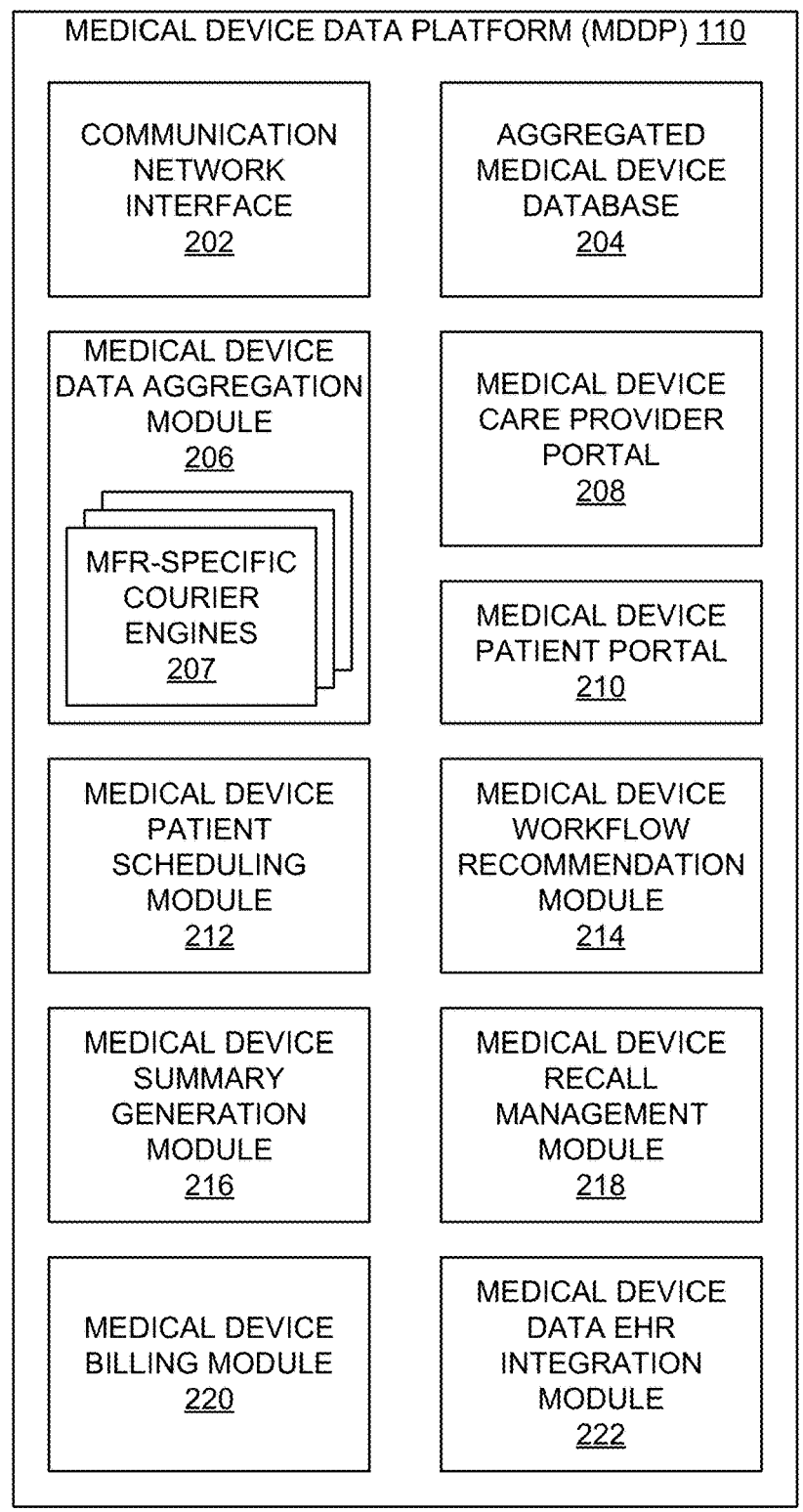
FIG. 2 is a block diagram of the example medical device data platform of FIG. 1.

FIG. 2 is a block diagram of the example MDDP 110 of FIG. 1. As depicted in FIG. 2, the MDDP 110 may include one or more of a communication network interface 202, an aggregated medical device database 204, a medical device data aggregation module 206, a medical device care provider portal 208, a medical device patient portal 210, a medical device patient scheduling module 212, a medical device workflow recommendation module 214, a medical device summary generation module 216, a medical device recall management module 218, a medical device billing module 220, and a medical device data electronic health record (EHR) integration module 222. Other modules not specifically described herein may also be included in the MDDP 110 in other examples. Further, each of these modules may be incorporated within the integration server 112 and/or the core cloud 114, as depicted in FIG. 1.

The communication network interface 202 may be configured to facilitate communication between the MDDP 110 and the implantable medical device manufacturer systems 120, the clinic systems 130, and any patient communication systems or devices. Embodiments of the communication network interface 202 may include an interface to the Internet or another wide area network (WAN) that presents, for example, a patient web portal through which patients may access processed diagnostic information and other data related to their implanted medical devices, and a provider web portal through which clinic staff 101 may access the processed information corresponding to implantable medical devices of their patients. The communication network interface 202 may also facilitate access to diagnostic and related information from each of the plurality of implantable medical devices stored at each of the manufacturer systems 120 according to the data format and associated communication protocols of each manufacturer system 120.

The aggregated medical device database 204 may store the diagnostic information and related data from the implantable medical devices that was retrieved from the manufacturer systems 120, as well as store the processed versions of that information. The aggregated medical device database 204 also may store other types of information, such as, for example, implantable medical device recall information, clinic workflow recommendation data, and so on.

The medical device data aggregation module 206 may be located in the integration server 112 and configured to retrieve the diagnostic and other device-related data from each of the manufacturer systems 120 by way of a corresponding manufacturer-specific courier engine 207. In an example, each of the manufacturer-specific courier engines 207 may retrieve the data via the communication network interface 202 using the particular security measures, communication protocols, data formats, and other characteristics of the specific manufacturer system 120 required to retrieve the data therefrom. Moreover, each of the manufacturer-specific courier engines 207 may convert the retrieved data into a unified format that is applied to the data received from all of the manufacturer systems 120 so that the core cloud 114 may process the device data to yield patient-oriented information and/or provider-oriented information in a consistent manner. In at least some examples, the use of the medical device data aggregation module 206 may reduce the need for in-clinic information technology (IT) specialists to retrieve the diagnostic data and other information from the implantable medical devices, especially for devices from multiple manufacturers, each of which may employ their own data formats, communication protocols, and the like.

The medical device care provider portal 208 may be configured to present a web interface to the clinic systems 130 that facilitates access by clinic staff 101 to the provider-oriented device data information corresponding to the patients of that clinic. Similarly, the medical device patient portal 210 may be configured to provide a separate web interface to the patients of a particular clinic, or to the patients of implantable medical devices in general. The medical device care provider portal 208 and the medical device patient portal 210 may require a log on of the clinic staff 101 and the patient, respectively, to allow access to the provider-oriented or patient-oriented information, as appropriate. In some examples, logging on to medical device care provider portal 208 may facilitate access by clinic staff 101 to other systems external to or located within the clinic system 130 (e.g. the EMR system 132 and the HIE system 134 of FIG. 1) via single sign-on (SSO) functionality, as mentioned above. In addition, the medical device care provider portal 208 and/or the medical device patient portal 210 may provide an application programming interface (API) that facilitates patient or provider access to electronic health records (EHRs) of the patient that may contain access points, such as, for example, embedded web links, to the device-related information.

In other examples, the MDDP 110 may provide or include other information portals aside from the medical device care provider portal 208 and the medical device patient portal 210, such as, for example, portals for administrative personnel associated with a clinic or insurance company, executives associated with a clinic or insurance company, employees of one or more cardiac device manufacturers, and so on. In such examples, each particular class or group of potential users of the MDDP 110 may be associated with a particular access scope or set of access rights, set of security requirements (e.g., requirements for user names, passwords, computer systems, etc.). As a result, each group of users may employ a corresponding user portal similar to the provider portal 208 and/or the patient portal 210. Each particular portal may be accessible by way of different Uniform Resource Locators (URLs), or may be distinguished in one or more other ways.

The medical device patient scheduling module 212 may be configured to present a web interface (e.g., the web portals described above, or a separate web portal) accessible to patients and/or clinic staff 101 to schedule appointments, such as in-office or in-home device check or programming visits, with clinic patients. In some examples, the scheduling web portal may be customized for each particular clinic, possibly providing additional information regarding services rendered by the clinic, descriptions of the members of the clinic staff 101, and so on.

The medical device workflow recommendation module 214 may be configured to monitor information regarding periodic device checks, the resulting diagnostic data, and other information related to the implantable medical devices of one or more patients, and based on that information, recommend changes to the workflow of the clinic, such as, for example, changes to device check schedules, changes to the particular types of information retrieved from the implantable medical device, changes to how the retrieved information is processed, and the like, thus possibly rendering the operations of the clinic more efficient.

The medical device summary generation module 216 may be configured to process the diagnostic and related information retrieved from the implantable medical devices via the associated manufacturer systems 120 to generate summary information regarding the functionality of the devices. In some examples, the resulting summary information may be in the form of patient-oriented information, which may be of particular use to laypeople, and/or in the form of provider-oriented information, which may be more technical and detailed in nature relative to the patient-oriented information, thus providing more useful information from the perspective of the care provider. Such information may include, for example, diagnostic information (e.g., passing or failing status of one or more tests, measured electrical voltage and/or current levels, and so on) describing the technical or operational status of the device, the health or biological response of the patient to the operation of the device based on data detected by the device (e.g., pulse rate, electrogram (EGM) data, and/or other signals detected at the device), and so on.

The medical device recall management module 218 may be configured to provide (e.g., "push") timely notifications and more detailed information to clinic staff 101 regarding recalls of implantable medical devices associated with that clinic. As mentioned above, the medical device recall management module 218 may collect information from one or more sites, such as, for example, official federal governing bodies, state and/or national medical boards, news agencies, and so on, and generate recall information, collect such information in the recall advisory registry database 146, and provide notifications regarding discovered recalls of implantable medical devices based on the information in the recall advisory registry database 146 by way of, for example, e-mail, text, patient-oriented web portal, and/or provider-oriented web portal corresponding to each affected clinic.

The medical device billing module 220 may be configured to present an interface (e.g., via the provider-oriented web portal) through which clinical staff 101 may enter an indication of one or more clinical actions taken with respect to an implantable medical device of a patient, and in which a currently appropriate billing code representing that action is generated. Further, the resulting billing codes for one or more such actions may further be inserted into a billing code summary sheet or other format for presentation to the patient, medical insurance company, and so on. In some examples, the medical billing code module 220 may receive or retrieve information regarding changes in billing codes from the Centers for Medicare and Medicaid Services (CMS) employable in a prospective payment system (PPS) and utilize those changes to update the billing codes corresponding to clinical actions related to implantable medical devices.

The medical device data EHR integration module 222 may be configured to update or populate EHRs with processed diagnostic data and other information related to implantable medical devices (e.g., the EMR data 138 of FIG. 1) by, for example, embedding web links into the EHR of a patient that facilitate access to the processed device-related data. Such data may include, for example, dates of the diagnostics performed on the implantable medical device, numerical data and/or graphs of the diagnostics results, recommended and/or performed actions based on the diagnostic results, the health or biological response of the patient to the operation of the device based on data detected by the device, and so on.

Figure 3:
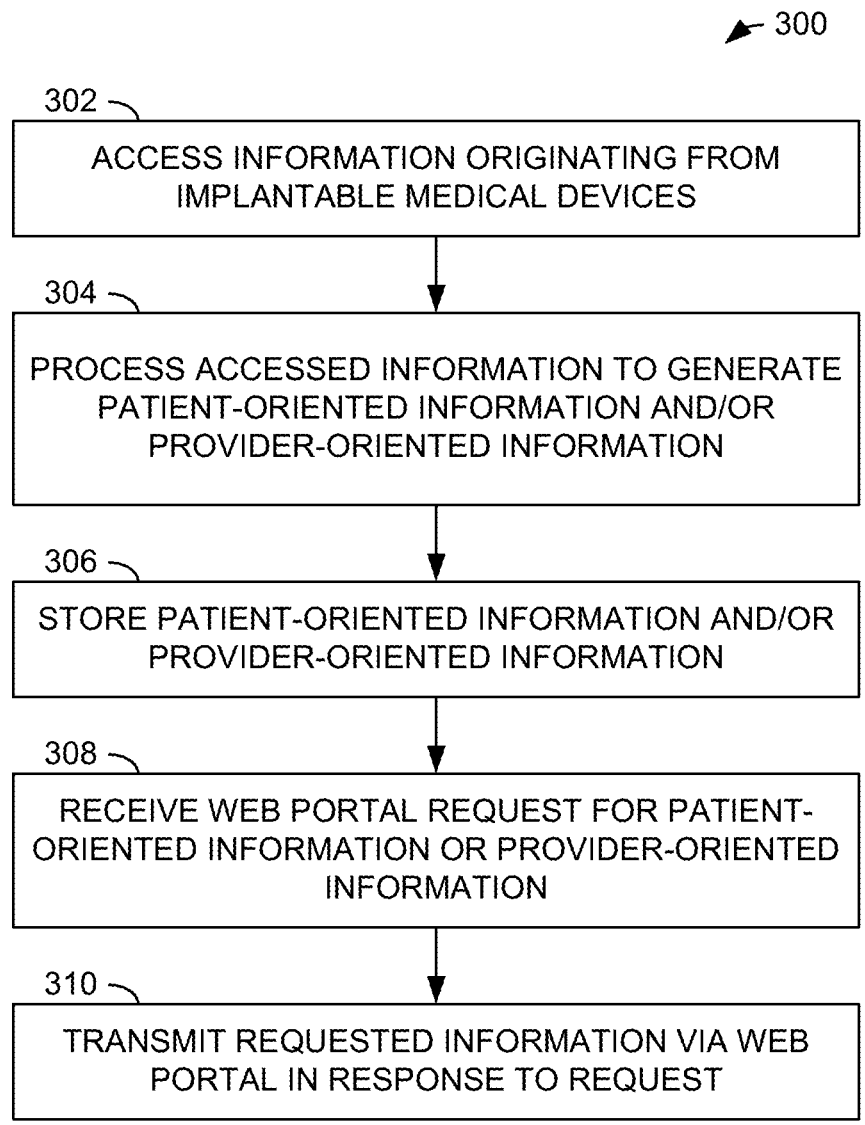
FIG. 3 is a flow diagram of an example method of providing patient-oriented and/or provider-oriented information via a web portal.

FIG. 3 is a flow diagram of an example method 300 of providing patient-oriented and/or provider-oriented information via a web portal. While the method 300 is presumed in the following description to be performed by the MDDP 110 of FIG. 1, other systems or devices may be employed to perform the method 300 in other examples.

In the method 300, the integration server 112 of FIG. 1 may access information (e.g., diagnostic data and/or other related information) originating from a plurality of implantable medical devices (operation 302). In one example, the information may be accessed from each of a plurality of manufacturer systems 110 that store the information previously retrieved from the implantable medical devices associated with the corresponding manufacturer. In other embodiments, the integration server 112 may retrieve the information more directly from the implantable medical devices without the involvement of manufacturer systems 110.

The core cloud 114 (or, alternatively, the integration server 112) may process the accessed information to generate patient-oriented information and/or provider-oriented information (operation 304), as discussed above. The generated information may be stored at the core cloud 114, or at some database accessible via the core cloud 114 (operation 306).

The core cloud 114 may receive a request via a web portal for at least some portion of the patient-oriented information or the provider-oriented information (operation 308). In response to the request, the core cloud 114 may transmit the corresponding device information via the web portal (operation 310).

While the operations 302 through 310 are shown as being performed in a particular order, other orders of performance for the operations 302 through 310 are also possible. For example, the accessing (operation 302), processing (operation 304), and storing (operation 306) of information may occur concurrently with the reception of the request for previously stored data (operation 308) and the transmission of the requested data via the web portal (operation 310). Other orders of performance of the operations 302 through 310 may also be possible, as well as that of other methods described herein.

Figure 4:
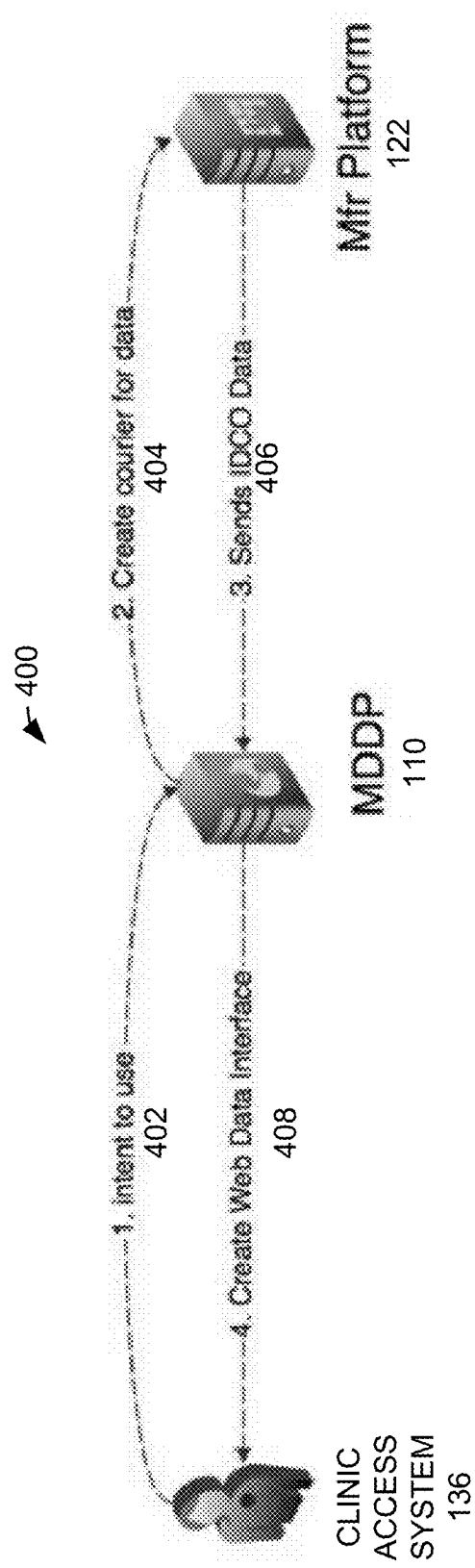
FIG. 4 is a communication diagram for an example method of initializing access to provider-oriented information by a clinic via a web portal.

FIG. 4 is a communication diagram for an example method 400 of initializing access to provider-oriented information by a clinic via a web portal. In the method 400, the clinic access system 136 may transmit to the MDDP 110 an intention to use a provider web portal provided by the MDDP 110 (e.g., the core cloud 114 of FIG. 1) (operation 402). The intention may be, for example, a request from clinic staff 101 to create an account or logon on the MDDP 110 for the associated clinic.

In response to the intention or request, the MDDP 110 (or, more specifically, the integration server 112) may create a manufacturer-specific courier engine 207 for each manufacturer of each implantable medical device that may be provided and/or monitored by the clinic, if such a courier engine does not currently exist. In some examples, a courier engine 207 may be generated for each pairing of a clinic and an associated manufacturer system 120, as different clinics may require different types or sets of information to be retrieved from the implantable medical devices, or different clinic systems 130 or manufacturer systems 120 may employ different, specific security measures for accessing the implantable medical device data.

The resulting courier engine 207 may then issue one or more requests to retrieve device-related data (e.g., device diagnostics data) from the manufacturer platform 122 of the particular manufacturer system 120 (operation 404). In response to the one or more requests, the manufacturer platform 122 may return the requested data originating from one or more implantable medical devices associated with the clinic to the MDDP 110 (operation 406). In some examples, the device data may be formatted as multiple IDCO messages, or enhanced or augmented IDCO messages, as mentioned above. The MDDP 110 (or, more specifically, the core cloud 114) may process and subsequently store the received device data as provider-oriented and/or patient-oriented information.

The MDDP 110 may also create a provider web portal or web data interface to be accessed via the clinic access system 136 (operation 408). In at least some examples, the provider web portal may be generated in response to the intention previously received (operation 402). In other examples, the intention first may be verified or authorized, such as by way of the manufacturer platform 122 or another system, prior to the generation of the web portal. After generation of the web portal, clinic staff 101 may employ the clinic access system 136 to access the previously processed device data from the MDDP 110 via the portal. In some examples, the MDDP 110, via the core cloud 114, may provide such information as EMR data 114 to the one or more EMR systems 132 so that the processed information originating from the retrieved medical device data may accessible via the EMRs of each corresponding patient.

Those skilled in the art will understand and appreciate that various modifications not explicitly described above may be made to the present disclosure and still remain within the scope of the present invention.

The resulting medical device data access system embodiments disclosed herein may be advantageous for several reasons. For example, the process described above of obtaining diagnostic information and other data stored within implantable medical devices, which number in the millions globally, may be automatically facilitated across all manufacturers, clinics, and patients, thus reducing the need for additional IT personnel to be involved with the periodic uploading and analysis of device data. In some embodiments, the processed data may be integrated with existing patient EHRs or EMRs to facilitate simplified access to that data by the patient or care provider. In addition, the medical device data access system may provide analytics, device recall management, billing code generation, and other advanced features, as described above, to improve or enhance the user (e.g., patient or care provider) experience.

Figure 5:
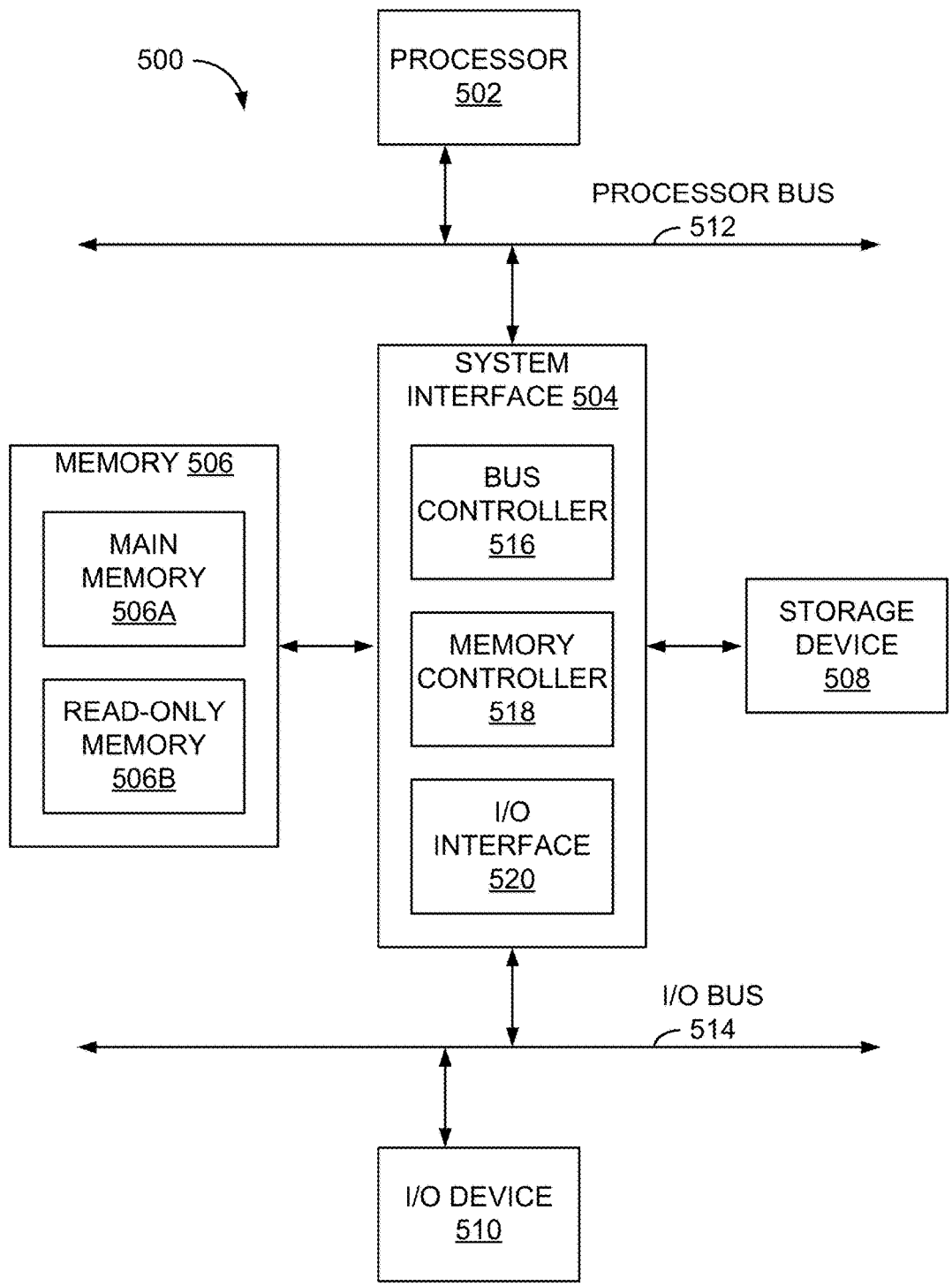
FIG. 5 is block diagram illustrating an example of a computing system which may be used in implementing embodiments of the present disclosure.

FIG. 5 is a block diagram illustrating an example of a computing device or computer system 500 which may be used to implement the embodiments disclosed above, such as, for example, the core cloud 114 and/or the integration server 112 of the MDDP 110 described earlier. Embodiments disclosed herein include various operations that maybe performed by hardware modules or components, or hardware modules or components used in combination with software instructions. Moreover, as described herein, in some embodiments, a first module or component may be hardware that is programmed by one set of software or firmware instructions to perform one or more functions, while a second module or component may be that same hardware that is programmed by another set of software or firmware instructions to perform one or more other functions. As a result, the same hardware may represent the first module during one period of time, and may represent the second module during the same time or a second period of time. According to one example, the computing device or system 500 may include at least one processor 502, at least one system interface 504, at least one memory 506, at least one storage device 508, and at least one I/O device 510. The system 500 may further include at least one processor bus 512 and/or at least one input/output (I/O) bus 514.

The processor 502 may include one or more internal levels of cache (not shown in FIG. 5) and can be any known processor, such as a microprocessor, microcontroller, digital signal processor, graphics processor, or the like. The processor bus 512, also possibly known as a host bus or a front side bus, may be used to couple the processor 502 with the system interface 504. The system interface 504 may be connected to the processor bus 512 to interface various components of the system with the processor 502. System interface 504 may, for example, include a bus controller 516 or bus interface unit to direct interaction with the processor bus 512 and a memory controller 518 for interfacing the memory 506 with the processor bus 512. The system interface 504 may also include an I/O interface 520 to interface one or more I/O devices 510 with the processor 502.

The memory 506 may include one or more memory cards and control circuits (not depicted in FIG. 5). The memory 506 may include a main memory 506A and/or a read-only memory (ROM) 506B. The main memory 506A can be random access memory (RAM) or any other dynamic storage device(s) for storing information and instructions to be executed by the processor 502. Main memory 506A may be used for storing temporary variables or other intermediate information during execution of instructions by the processor 502. The read-only memory 506B can be any static storage device(s), such as Programmable Read Only Memory (PROM) chip for storing static information and instructions for the processor.

According to one embodiment, the above methods may be performed by the computer system 500 in response to the processor 502 executing one or more sequences of one or more instructions contained in the main memory 506A. These instructions may be read into main memory 506A from another machine-readable medium capable of storing or transmitting information in a form (e.g., software, processing application) readable by a machine (e.g., a computer). Execution of the sequences of instructions contained in the main memory 506A may cause the processor 502 to perform the process operations described herein.

A machine-readable media may take the form of, but is not limited to, non-volatile media and volatile media. Non-volatile media may include a mass storage device 508 and volatile media may include dynamic storage devices. Common forms of machine-readable media may include, but are not limited to, magnetic storage media (e.g. hard disk drive); optical storage media (e.g. Compact Disc Read-Only Memory (CD-ROM) and Digital Versatile Disc Read-Only Memory (DVD-ROM)), magneto-optical storage media; read-only memory (ROM); random access memory (RAM, such as static RAM (SRAM) and dynamic RAM (DRAM)); erasable programmable memory (e.g., erasable programmable read-only memory (EPROM) and electrically erasable programmable read-only memory (EEPROM)); flash memory; or other types of media suitable for storing computer or processor instructions.

Embodiments disclosed herein include various operations that are described in this specification. As discussed above, the operations may be performed by hardware components and/or may be embodied in machine-executable instructions, which may be used to cause a general-purpose or special-purpose processor programmed with the instructions to perform the operations. Alternatively, the operations may be performed by a combination of hardware, software, and/or firmware.

The performance of one or more operations described herein may be distributed among one or more processors, not only residing within a single machine, but deployed across a number of machines. In some examples, the one or more processors or processor-implemented modules may be located in a single geographic location (e.g., within a home environment, an office environment, or a server farm). In other embodiments, the one or more processors or processor-implemented modules may be distributed across a number of geographic locations.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores may be arbitrary, and particular operations are illustrated in a context of specific illustrative configurations. In general, structures and functionality presented as separate resources in the examples configurations may be implemented as a combined structure or resource. Similarly, structures and functionality presented as a single resource may be implemented as separate resources.

While the present disclosure has been described with reference to various embodiments, these embodiments are illustrative, and the scope of the disclosure is not limited to such embodiments. Various modifications and additions can be made to the exemplary embodiments discussed herein without departing from the scope of the disclosure. For example, while the embodiments described above refer to particular features, the scope of this disclosure also includes embodiments having different combinations of features, as well as embodiments that do not include all of the described features. Accordingly, the scope of the disclosure is intended to embrace all such alternatives, modifications, and variations, together with all equivalents thereof.

What is claimed is:

1. A medical device data platform comprising:
    at least one integration device accessing information originating from a plurality of implantable medical devices, the plurality of implantable medical devices being manufactured by a plurality of manufacturers and implanted in a plurality of patients, the at least one integration device accessing the information according to a data format and one or more associated communications protocols specific to each of the plurality of manufacturers, the at least one integration device converting the information from the respective data formats into a unified format;
    a core cloud having at least one processor, the core cloud processing the information in the unified format to generate provider-oriented information for the plurality of implantable medical devices; and
    a provider portal accessible with at least one communication device, the provider portal providing a portion of the provider-oriented information corresponding to a subset of the plurality of implantable medical devices, the subset of the plurality of implantable medical devices being for a group of the plurality of patients associated with at least one care provider, the portion of the provider-oriented information including care provider analytics for the at least one care provider.

2. The medical device data platform of claim 1, wherein the provider-oriented information comprises biological response data of at least one of the plurality of patients from the group.

3. The medical device data platform of claim 1, wherein the provider-oriented information comprises a technical status of at least one of the plurality of implantable medical devices from the subset.

4. The medical device data platform of claim 1, wherein the provider-oriented information comprises recall information corresponding to at least one of the plurality of implantable medical devices from the subset.

5. The medical device data platform of claim 1, wherein the core cloud schedules appointments for at least one of the plurality of patients.

6. The medical device data platform of claim 1, wherein the care provider analytics comprise at least one recommended change to a workflow of at least one care provider.

7. The medical device data platform of claim 1, wherein the provider portal obtains an identification of clinical actions taken by the at least one care provider with respect to at least one of the subset of the plurality of implantable medical devices.

8. The medical device data platform of claim 7, wherein one or more billing codes are generated for the clinical actions.

9. The medical device data platform of claim 1, wherein the at least one integration device accesses the information directly from the plurality of implantable medical devices over a communication network.

10. The medical device data platform of claim 1, wherein the at least one integration device accesses the information over a communication network from respective manufacturer platforms of the plurality of manufacturers.

11. The medical device data platform of claim 1, wherein the core cloud further processes the information in the unified format to generate patient-oriented information.

12. The medical device data platform of claim 11, wherein the provider portal updates electronic medical records of at least one of the plurality of patients from the group with at least one of the patient-oriented information and the provider-oriented information.

13. The medical device data platform of claim 1, wherein the at least one communication device further provides a patient portal configured to provide, to each of the plurality of patients, at least a portion of the patient-oriented information corresponding to at least one of the plurality of implantable medical devices associated with the patient.

14. A method comprising:
    accessing information originating from a plurality of implantable medical devices using at least one integration device, the plurality of implantable medical devices being manufactured by a plurality of manufacturers and implanted in a plurality of patients, the information being accessed according to a data format and one or more associated communications protocols specific to each of the plurality of manufacturers;
    converting the information from each of the data formats into a unified format using the at least one integration device;
    generating provider-oriented information for the plurality of implantable medical devices by processing the information the unified format using at least one processor of a core cloud;
    providing a portion of the provider-oriented information with a provider portal accessible with at least one communication device, the portion of the provider-oriented information corresponding to a subset of the plurality of implantable medical devices for a group of the plurality of patients associated with at least one care provider, the portion of the provider-oriented information including care provider analytics for the at least one care provider.

15. The method of claim 14, wherein the provider-oriented information comprises recall information corresponding to at least one of the plurality of implantable medical devices from the subset.

16. The method of claim 14, further comprising:
   obtaining an identification of clinical actions taken by the at least one care provider with respect to at least one of the subset of the plurality of implantable medical devices.

17. The method of claim 16, further comprising:
   generating one or more billing codes for the clinical actions.

18. The method of claim 14, wherein the care provider analytics comprise at least one recommended change to a workflow of at least one care provider.

19. The method of claim 14, wherein the at least one integration device accesses the information over a communication network from respective manufacturer platforms of the plurality of manufacturers.

20. The method of claim 14, wherein the at least one integration device accesses the information over a communication network from respective manufacturer platforms of the plurality of manufacturers.

21. The method of claim 14, further comprising:
   scheduling appointments for at least one of the plurality of patients.

* * * * *